US00PP17490P2

(12) United States Plant Patent
Bontekoe

(10) Patent No.: US PP17,490 P2
(45) Date of Patent: Mar. 13, 2007

(54) ***SALIX* PLANT NAMED 'FLAMINGO'**

(50) Latin Name: *Salix integra*
Varietal Denomination: Flamingo

(76) Inventor: Peter B. W. Bontekoe, De Oude Wijk 7, 2771 WT Boskoop (NL)

( * ) Notice: Subject to any disclaimer, the term of this patent is extended or adjusted under 35 U.S.C. 154(b) by 0 days.

(21) Appl. No.: 11/204,328

(22) Filed: Aug. 15, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
(74) *Attorney, Agent, or Firm*—C. A. Whealy

(57) ABSTRACT

A new and distinct cultivar of *Salix* plant named 'Flamingo', characterized by its upright and outwardly spreading growth habit; small and durable leaves; developing leaves that are pinkish red in color; fully expanded leaves that are green and greenish white variegated; leaves that resist sunburning; and thick pink to red-colored stems.

2 Drawing Sheets

Botanical designation: *Salix integra.*
Cultivar denomination: 'Flamingo'.

BACKGROUND OF THE INVENTION

The present Invention relates to a new and distinct cultivar of *Salix* plant, botanically known as *Salix integra,* and hereinafter referred to by the cultivar name Flamingo.

The new *Salix* is a naturally-occurring whole plant mutation of the *Salix integra* cultivar Hakuro Nishiki, not patented. The new *Salix* was discovered and selected by the Inventor as a single plant within a population of plants of the cultivar Hakuro Nishiki in May, 1996 in a controlled environment in Boskoop, The Netherlands.

Asexual reproduction of the new cultivar by terminal cuttings in a controlled environment in Boskoop, The Netherlands since January, 2003, has shown that the unique features of this new *Salix* are stable and reproduced true to type in successive generations.

SUMMARY OF THE INVENTION

Plants of the cultivar Flamingo have not been observed under all possible environmental conditions. The phenotype may vary somewhat with variations in environment such as temperature and light intensity without, however, any variance in genotype.

The following traits have been repeatedly observed and are determined to be the unique characteristics of 'Flamingo'. These characteristics in combination distinguish 'Flamingo' as a new and distinct cultivar of *Salix:*

1. Upright and outwardly spreading growth habit.
2. Small and durable leaves.
3. Developing leaves pinkish red in color; fully expanded leaves, green and greenish white variegated.
4. Leaves that resist sunburning.
5. Thick pink to red-colored stems.

Plants of the new *Salix* can be compared to plants of the parent, the cultivar Hakuro Nishiki. In side-by-side comparisons conducted in Boskoop, The Netherlands, plants of the new *Salix* differed from plants of the cultivar Hakuro Nishiki in the following characteristics:

1. Plants of the new *Salix* had a more upright growth habit than plants of the cultivar Hakuro Nishiki.
2. Plants of the new *Salix* had smaller and thinner leaves than plants of the cultivar Hakuro Nishiki.
3. Plants of the new *Salix* had thicker stems than plants of the cultivar Hakuro Nishiki.
4. Developing leaves and stems of plants of the new *Salix* were more red in color than developing leaves and stems of plants of the cultivar Hakuro Nishiki.
5. Leaves of plants of the new *Salix* resisted sunburning whereas leaves of plants of the cultivar Hakuro Nishiki sunburned.

Plants of the new *Salix* can also be compared to plants of the *Salix integra* cultivar Pendula, not patented. Plants of the new *Salix* differ primarily from plants of the cultivar Pendula in plant shape as plants of the cultivar Pendula have cascading stems.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Salix.*

The photograph at the top of the first sheet comprises a side perspective view of a typical plant of 'Flamingo' grown in a container.

The photograph at the bottom of the first sheet is a close-up view of a typical plant of 'Flamingo'.

The photographs on the second sheet are close-up views of typical stems and leaves of 'Flamingo'.

DETAILED BOTANICAL DESCRIPTION

The aforementioned photographs and following observations and measurements describe plants grown in Boskoop, The Netherlands in an outdoor nursery during the late spring with day temperatures ranging from 7° C. to 25° C. and night temperatures ranging from 4° C. to 14° C. Plants were grown in containers and had been growing for about two years in 19-cm containers when the photographs and description were taken. Plants were pinched one time. Color references are made to The Royal Horticultural Society Colour Chart, 2001 Edition, except where general terms of ordinary dictionary significance are used.

Botanical classification: *Salix integra* cultivar Flamingo.

Parentage: Naturally-occurring whole plant mutation of the *Salix integra* cultivar Hakuro Nishiki, not patented.

Propagation:

*Type cutting.*—Vegetative cuttings.

*Time to initiate roots, summer.*—About 20 days at 20° C.

*Time to initiate roots, winter.*—About 25 days at 15° C.

*Time to produce a rooted young plant.*—About six months at 10° C. to 30° C.

*Root description.*—Fibrous; white in color.

Plant description:

*Form.*—Upright and outwardly spreading growth habit; globular. Freely branching growth habit; dense and bushy appearance. Moderately vigorous growth habit.

*Plant height.*—About 1.75 meters.

*Plant diameter.*—About 1.75 meters.

*Lateral branches.*—Length: About 16 cm. Diameter: About 3 mm. Internode length: About 2.5 cm. Strength: Moderately strong. Texture: Smooth, glabrous. Color, developing stems: 143B overlain with close to 186A. Color, fully developed stems: 143B overlain with close to 175A to 175B.

*Foliage description.*—Arrangement: Alternate; simple; sessile. Length: About 4.2 cm. Width: About 1.7 cm. Shape: Elliptic-oblong to ovate. Apex: Acute. Base: Cuneate. Margin: Entire. Texture, upper and lower surfaces: Smooth, glabrous. Venation pattern: Pinnate. Color: Developing foliage, upper and lower surfaces: Close to 37B to 37C; venation, 52B. Fully expanded foliage, upper surface: Random sectors, areas and spots of 137A, N144C, 145D and 157D; venation, 194B with a pink blush. Leaves resistant to sunburning. Fully expanded foliage, lower surface: Random sectors, areas and spots of 137B to 137C, N144C, 145D and 157D; venation, 194B with a pink blush. Venation, upper surface: 146C. Venation, lower surface: 137A.

Flower description: Flower development has not been observed on plants of the new *Salix*.

Disease/pest resistance: Plants of the new *Salix* have not been noted to be resistant to pathogens or pests common to *Salix*.

Temperature tolerance: Plants of the new *Salix* have been observed to tolerate temperatures from −10° C. to 35° C.

It is claimed:

1. A new and distinct cultivar of *Salix* plant named 'Flamingo', as illustrated and described.

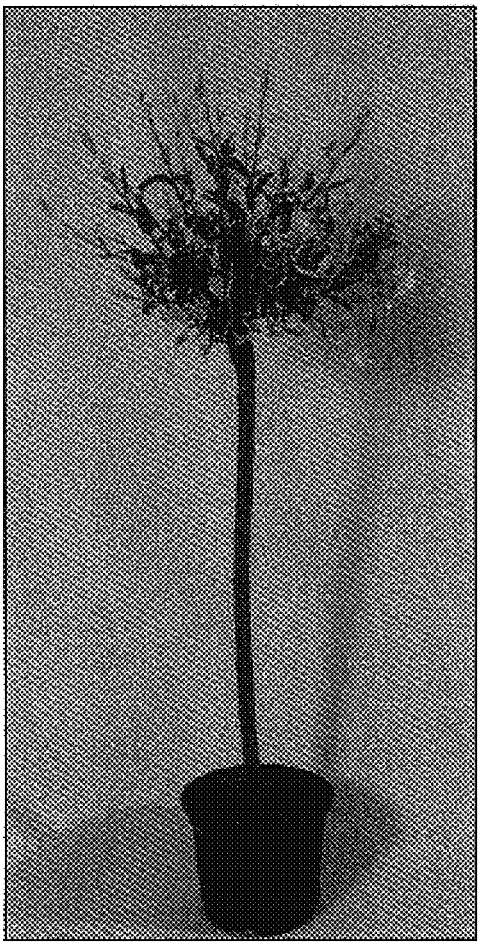
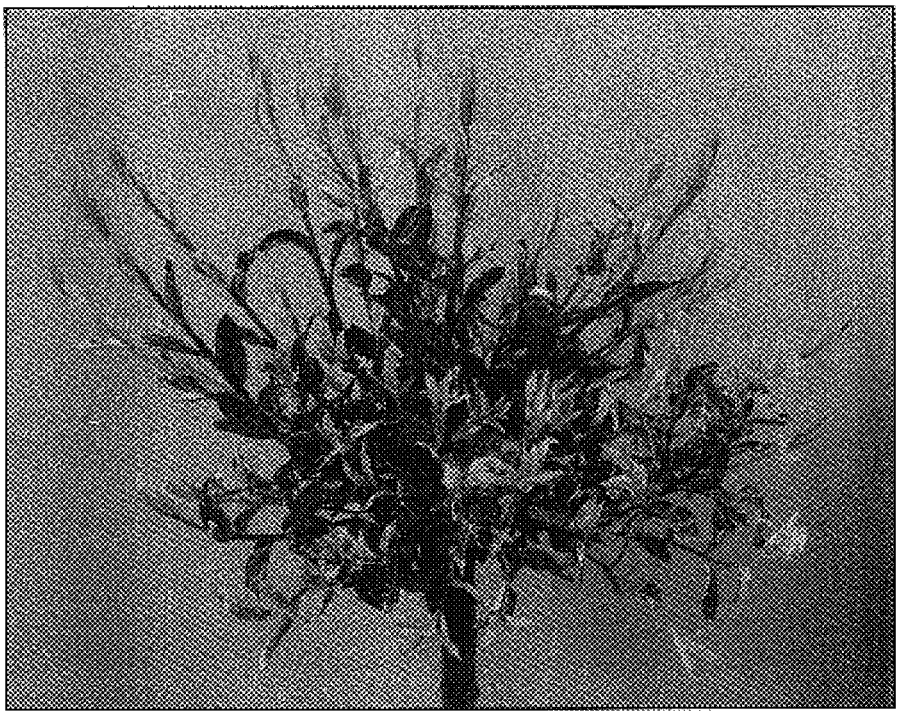

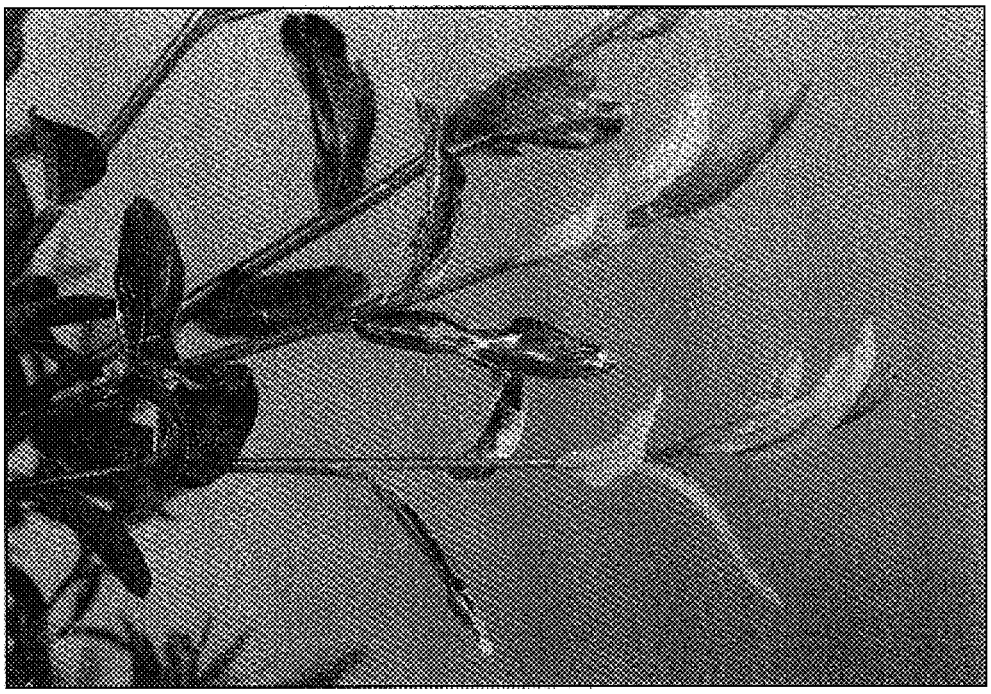
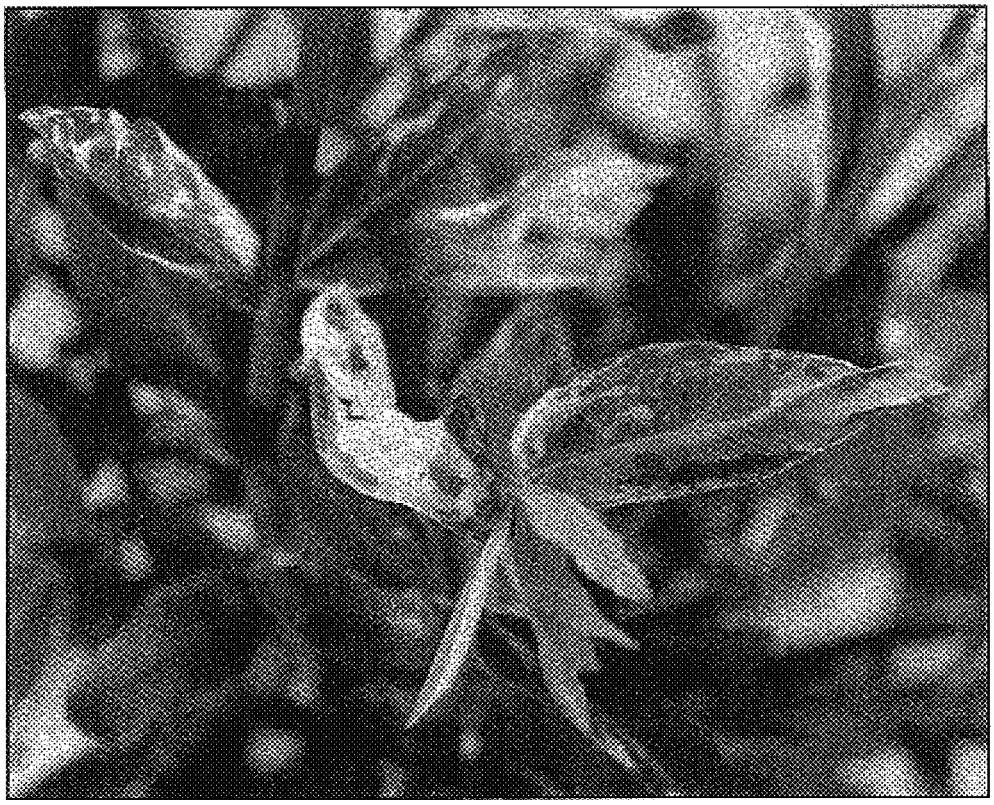

* * * * *